United States Patent [19]  
Jones

[11] 4,164,139  
[45] Aug. 14, 1979

[54] ASPHALT PENETRATION INDICATOR

[75] Inventor: George M. Jones, Salt Lake City, Utah

[73] Assignee: The Gilsabind Company, Mack, Colo.

[21] Appl. No.: 932,225

[22] Filed: Aug. 9, 1978

[51] Int. Cl.² .................................................. G01N 15/08
[52] U.S. Cl. .................................................. 73/38
[58] Field of Search ........................................ 73/38

[56] References Cited

U.S. PATENT DOCUMENTS

| 2,310,111 | 2/1943 | Nordlander | 73/38 X |
| 3,371,519 | 3/1968 | Slone et al. | 73/38 |
| 3,548,635 | 12/1970 | Hutchinson et al. | 73/38 |
| 3,861,196 | 1/1975 | Domenighetti | 73/38 |
| 4,070,903 | 1/1978 | Lees et al. | 73/38 |

Primary Examiner—Daniel M. Yasich  
Attorney, Agent, or Firm—Criddle, Thorpe & Western

[57] ABSTRACT

Water penetration of bituminous pavement is measured by a conduit comprising a cylindrical tube having a flat outwardly extending lower flange and a closed top having a circular center opening into which is engaged an upwardly extending graduated cylinder open at both ends having a diameter significantly smaller than the cylindrical tube. The flat lower rim is adapted to hold a sealant on its lower surface and a weight having a central opening fitted around the cylindrical tube on its upper surface. The weight causes the sealant to seal the apparatus to the pavement in a fluid tight relationship and when the apparatus is filled with water the degree of water penetration into the pavement can be determined by the change of water volume in the graduated cylinder.

6 Claims, 3 Drawing Figures

ASPHALT PENETRATION INDICATOR

BACKGROUND OF THE INVENTION

This application relates to an apparatus for determining the degree of water penetration into bituminous pavement.

Water penetrates open bituminous pavement and infiltrates between the bituminous cement and the mineral aggregate thus breaking the bond between them. Also in cold weather, the freeze-thaw cycles of water in the pavement and the action of chemicals, such as sodium chloride, spread on paved areas to prevent freezing accelerates this condition. When this action becomes extensive the pavement fails and pot holes or other forms of asphaltic deterioration develop causing extensive damage to roads or other paved areas.

For asphaltic pavements built on well graded bases most of the moisture enters the pavement from the surface. Sealing the surface with various types of sealants stops or retards penetration of water and prolongs the life of the pavement.

To the present time there has been no effective means to determine whether or not a bituminous pavement should be sealed. Also, there has been no available method of evaluating the efficiency of a sealer.

BRIEF DESCRIPTION OF THE INVENTION

It is an object of this invention to provide an apparatus for determining the degree to which water will penetrate a bituminous pavement.

It is also an object of this invention to provide an apparatus which will indicate the effectiveness of a sealant applied to a bituminous pavement.

Another object of the present invention is to provide an apparatus which will directly measure the volume of water which will penetrate asphaltic cement when applied to a given area.

These and other objects may be accomplished by means of an apparatus consisting of two cylindrical tubes of different diameters joined together such that the lower tube has the greater diameter and contains an outwardly flaring rim or flange at the bottom thereof. The upper tube is significantly smaller in diameter and is graduated to indicate volume changes of water contained in that tube. A petroleum based sealant which may contain fiber reinforcement, is placed on the lower surface of the flange at the bottom of the larger tube and a weight, which surrounds the outside of the larger tube, rests on the top of the flange. The combination of the weight and the sealant creates a water tight seal between the apparatus and the bituminous pavement over which it is placed. By filling the apparatus with water and measuring the change in volume of water, as determined by the gradiations on the smaller tube, with respect to time the porosity of the pavement may be determined.

DETAILED DESCRIPTION OF THE INVENTION

Figure 1:
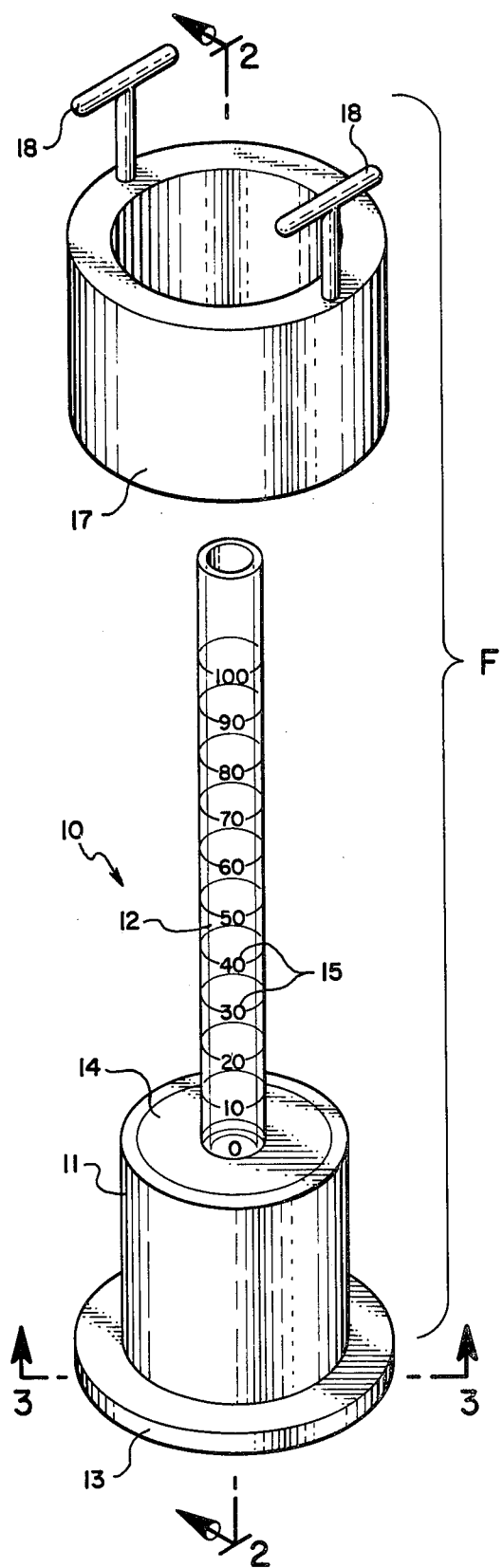
FIG. 1 is a perspective view of the apparatus with the weight being elevated ready to be lowered into position about the lower end of the conduit.
Figure 2:
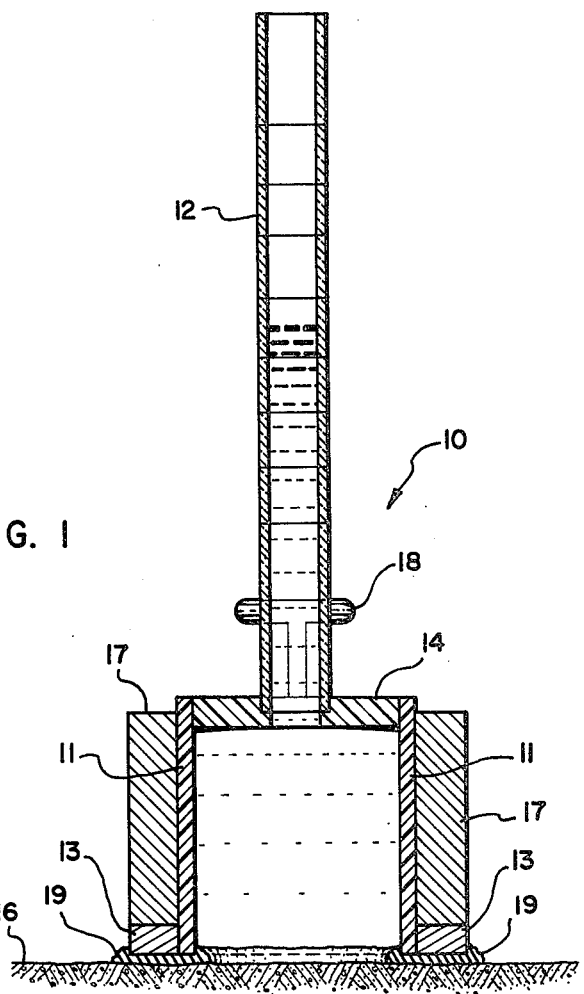
FIG. 2 is a cross sectional side view of the apparatus sealed to a bituminous pavement with the weight in place and taken along lines 2—2 of FIG. 1.
Figure 3:
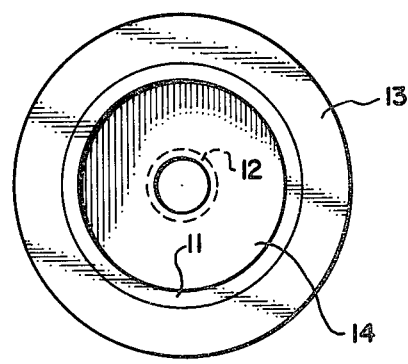
FIG. 3 is a bottom view of the conduit looking upward taken along line 3—3 of FIG. 1.

There is shown in FIGS. 1-3 a complete operative embodiment of the invention. The apparatus consists principally of two parts, a fluid restraining and measuring conduit and a weight surrounding and anchoring said conduit.

The conduit may be made of a single integrated unit or by a plurality of pieces cemented together. For purposes of illustration the conduit will be described in terms of a plurality of parts joined together in a fluid tight relationship.

The conduit 10 consists of two cylindrical tubes of different diameters. The larger diameter tube 11 will hereinafter be referred to as a "tube" and the smaller diameter tube 12 will be referred to as the "cylinder" or "graduated cylinder".

Tube 10 contains an outwardly extending flange 13 surrounding the bottom portion thereof and is partially enclosed at the top by a circular disc 14 having a circular central opening. A graduated cylinder 12 is inserted into the central opening and secured to circular disc 14. Conduit 10 is thus formed and has an open ended continuous passageway extending from the top of graduated cylinder 12 to the bottom of tube 11. Graduated cylinder 12 contains markings 15 along the length thereof corresponding to the difference in volume between the markings within the cylinder passageway. Such markings may be in any conventional volumetric units and are preferably used to measure milliliters.

Cylinder 12 is considerably smaller in diameter than tube 11 so that absorption of water from tube 11 will result in a greater vertical water displacement in cylinder 12. Preferably cylinder 12 will have a volumetric capacity of about 100 mls. and be about one inch in diameter. While there is no requirement that tube 11 be of any specific size it will normally have a diameter from three to six times as great as cylinder 12 and a height which approximates its diameter. At any rate the volumetric capacity of tube 11 must be at least as great as the volumetric capacity of cylinder 12 and will usually be several times greater.

Tube 11, flange 13 and circular disc 14 may be made of any clear or opaque material such as glass or any of the numerous thermoplastic resins. Graduated cylinder 12 may be made of the same materials but must be sufficiently transparent that the meniscus of water in the cylinder can be seen.

When the bottom of conduit 10 rests upon a flat paved surface 16 and the conduit is filled with water the conduit will not remain stationary. Therefore weight 17, being in the shape of an annular ring and having an inside diameter slightly larger than the outside diameter of tube 11, fits over the outside of tube 11 and rests against the upper edge of flange 13 holding conduit 10 in place on pavement 16. Preferably weight 17 has handles 18 for lifting the weight onto or off of the conduit. Weight 17 may be made of lead, steel or other high density material and must be heavy enough that when placed about the conduit the bottom surface of flange 13 will exert a pressure of at least about 1.5 psig on a corresponding paved bituminous surface.

In practice an area paved by a bituminous cement 16 selected for testing, is swept clean of all debris and dust. The bottom surface of flange 13 is covered with a plastic water resistant asphaltic cement 19 with a spatula. Preferably the covering is about ⅛ to ¼ inch thick. The conduit 10 is then pressed to the surface of the paved bituminous cement 16 at the selected site to a water tight seal. A small bead of asphaltic cement inside and outside the flange 13 indicates the supply of cement is adequate. Conduit 10 preferably contains a tube portion 11 having about a 4 inch diameter which is about 4 inches high and a 100 ml graduated cylinder 12 about one inch in diameter. Lead weight 17 weighing about 20 pounds is placed over the conduit and rests on the upper surface of flange 13. The conduit is then filled with water until the meniscus is at the 100 ml mark whereupon timing is begun.

Depending upon the rate of flow of water into the interstices of the pavement the permeation rate may be determined in two ways. If permeation is slow the change of volume is the graduated cylinder over a five minute period may be read directly. Since the area covered by the lower tube of the conduit may be readily determined by measurement of the diameter the results may be reported in terms of water absorption in milliliters per square inch of surface area for five minutes. If the loss of water is rapid the conduit may be filled above the graduated markings. When the water level reaches the 100 ml marking a stop watch may be started. Timing may be stopped when the water level reaches the 0 ml level of the graduated cylinder. The permeation rate may be reported in the same units as when the flow rate was slow by dividing 100 mls by the number of seconds to get the flow rate in terms of mls/sec., multiplying the result by 300 to obtain the number of mls which would permeate the pavement over a five minute period and divide that result by the area to obtain the water absorption in mls/in$^2$ of surface area for five minutes.

While the above is deemed to disclose a preferred embodiment of the invention changes may be made in structure and shape of the conduit without departing from the scope of the invention.

I claim:

1. An apparatus for measuring water penetration into a bituminous pavement which comprises
   (a) an integral conduit open at both ends consisting of a lower cylindrical tube portion of a given diameter containing an outwardly extending annular flange at the end thereof and an upper cylindrical tube portion of a lesser diameter, and
   (b) an annular weight adapted to fit around said lower cylindrical tube portion of said conduit and rest on the upper surface of the outwardly extending flange wherein the annular weight is sufficiently heavy that when a sealant is placed on the bottom surface the flange and the conduit is placed with the flange resting on a bituminous pavement the pressure exerted on the sealant by the annular weight is sufficient to seal the conduit to the bituminous pavement in a watertight relationship defining a watertight unit area such that water placed in said conduit will penetrate the pavement with the amount of penetration per unit area being determined by the change in water volume in the upper cylindrical tube portion of the conduit over a given period of time.

2. An apparatus according to claim 1 wherein the upper cylindrical tube portion of said conduit contains volumetric graduated markings.

3. An apparatus according to claim 2 wherein the diameter of the lower cylindrical tube portion of said conduit is from three to six times as great as the diameter of the upper cylindrical tube portion.

4. An apparatus according to claim 3 wherein the volumetric capacity of the lower cylindrical tube portion of said conduit is greater than the volumetric capacity of the upper cylindrical tube portion.

5. An apparatus according to claim 4 wherein the pressure exerted on the sealant is at least 1.5 psig.

6. An apparatus according to claim 4 wherein the annular weight contains handles.

* * * * *